US012791565B2

(12) United States Patent
Koos

(10) Patent No.: US 12,791,565 B2
(45) Date of Patent: Nov. 10, 2026

(54) METABOLIC PROFILE SCREENING FOR GESTATIONAL DIABETES

(71) Applicant: THE REGENTS OF THE UNIVERSITY OF CALIFORNIA, Oakland, CA (US)

(72) Inventor: Brian J. Koos, Marina Del Rey, CA (US)

(73) Assignee: THE REGENTS OF THE UNIVERSITY OF CALIFORNIA

( * ) Notice: Subject to any disclaimer, the term of this patent is extended or adjusted under 35 U.S.C. 154(b) by 1019 days.

(21) Appl. No.: 17/754,756

(22) PCT Filed: Oct. 9, 2020

(86) PCT No.: PCT/US2020/055020
§ 371 (c)(1),
(2) Date: Apr. 11, 2022

(87) PCT Pub. No.: WO2021/072222
PCT Pub. Date: Apr. 15, 2021

(65) Prior Publication Data

US 2024/0085432 A1 Mar. 14, 2024

Related U.S. Application Data

(60) Provisional application No. 62/914,294, filed on Oct. 11, 2019.

(51) Int. Cl.
*G01N 33/68* (2006.01)
*G01N 30/72* (2006.01)
(Continued)

(52) U.S. Cl.
CPC ....... *G01N 33/689* (2013.01); *G01N 30/7233* (2013.01); *G01N 33/5308* (2013.01);
(Continued)

(58) Field of Classification Search
CPC ............. G01N 33/689; G01N 30/7233; G01N 33/5308; G01N 2030/8813; G01N 2800/042; G01N 2800/368
See application file for complete search history.

(56) References Cited

U.S. PATENT DOCUMENTS

2013/0338031 A1* 12/2013 Hu ............................ A61P 9/10 435/7.92
2016/0341739 A1* 11/2016 Koos .................... G01N 33/689
2019/0310269 A1* 10/2019 Cirulli .................. G01N 33/743

FOREIGN PATENT DOCUMENTS

JP 2019027885 A 2/2019
WO WO2005058142 6/2005
(Continued)

OTHER PUBLICATIONS

Peters et al "Carnosinase, diabetes mellitus and the potential relevance of carnosinase deficiency" J Inherit Metab Dis (2018) 41:39-47. (Year: 2018).*
(Continued)

*Primary Examiner* — Dennis White
(74) *Attorney, Agent, or Firm* — Karen S. Canady; canady + lortz LLP

(57) ABSTRACT

Described herein are methods, materials, kits, devices, and assays for use in screening, detection, and treatment of diabetes, including diabetes mellitus and gestational diabetes mellitus (GDM). The amount of a plurality of metabolic markers present in a test sample obtained from the subject is measured, followed by comparing the amount of the metabolic markers present in the test sample to reference levels of the markers; and identifying a subject as susceptible to, or as having, diabetes when the amount of each of the measured markers present in the test sample is increased or decreased relative to the reference levels. Also provided is a method of treating diabetes in a subject when the amount of
(Continued)

each of the measured markers present in the test sample is increased or decreased relative to the reference levels.

19 Claims, 3 Drawing Sheets

(51) Int. Cl.
*G01N 30/88* (2006.01)
*G01N 33/53* (2006.01)

(52) U.S. Cl.
CPC ................ *G01N 2030/8813* (2013.01); *G01N 2800/042* (2013.01); *G01N 2800/368* (2013.01)

(56) References Cited

FOREIGN PATENT DOCUMENTS

| | | | | |
|---|---|---|---|---|
| WO | WO-2012058298 A1 * | 5/2012 | ......... | G01N 33/6848 |
| WO | WO2015109116 | 7/2015 | | |

OTHER PUBLICATIONS

Dostalek et al, "Diabetes Mellitus Reduces Activity of Human UDP-Glucuronosyltransferase 2B7 in Liver and Kidney Leading to Decreased Formation of Mycophenolic Acid Acyl-Glucuronide Metabolite" Drug Metabolism and Disposition vol. 39, Issue 3, Mar. 2011, pp. 448-455. (Year: 2011).*
Priyadarsini S, et al., Complete metabolome and lipidome analysis reveals novel biomarkers in the human diabetic corneal stroma. Exp Eye Res. Dec. 2016;153:90-100. doi: 10.1016/j.exer.2016.10.010. Epub Oct. 11, 2016. PMID: 27742548; PMCID: PMC5317205.
Office Action from corresponding Japan Application 2022-521574, dated Jun. 25, 2024, with English translation.
Medical Research Design and Statistical Analysis, edited by He Jia, Second Military Medical University Press, Sep. 2010, see pp. 104-129. Published in China.
Office Action from corresponding China Application 202080078823X, dated Jul. 22, 2023, with English translation.
Liu, Tianhu, et al., Comprehensive analysis of serum metabolites in gestational diabetes mellitus by UPLC/Q-TOF-MS. Anal Bioanal Chem. Feb. 2016;408(4):1125-35. doi: 10.1007/s00216-015-9211-3. Epub Dec. 16, 2015. PMID: 26677023.
Extended European Search Report from corresponding EP Application 20874333.6, dated Jan. 26, 2023.
Kappel, Ben, et al., (2017). Effect of Empagliflozin on the Metabolic Signature of Patients With Type 2 Diabetes Mellitus and Cardiovascular Disease. Circulation. 136. 969-972. 10.1161/CIRCULATIONAHA.117.029166.
Koos, Brian J et al., T-078—Gestational Diabetes Perturbs Energy Metabolism in Early Pregnancy. SRI 2020: Scientific Abstracts. Reprod. Sci. 27, (2020), 149A, Suppl 1. https://doi.org/10.1007/s43032-020-00176-9.
Koos, Brian J. et al., Early pregnancy metabolites predict gestational diabetes mellitus: implications for fetal programming, American Journal of Obstetrics & Gynecology, vol. 224, Issue 2, 215.e1-215.e7.
Murphy, Aisling, et al., O-005—Maternal Urinary Metabolites in the Latter Half of Pregnancy Predict Gestational Diabetes Mellitus., SRI 2020: Scientific Abstracts. Reprod. Sci. 27, (2020), 60A, Suppl 1. https://doi.org/10.1007/s43032-020-00176-9.
International Search Report and Written Opinion for PCT/US20/55020 (WO202107222 Published Apr. 15, 2021).
Borges Manna L, et al. First-trimester nuclear magnetic resonance-based metabolomic profiling increases the prediction of gestational diabetes mellitus. Am J Obstet Gynecol. Dec. 16, 2024:S0002-9378(24)01196-7. doi: 10.1016/j.ajog.2024.12.019. Epub ahead of print. PMID: 39694165.
Julkunen, H., et al. Atlas of plasma NMR biomarkers for health and disease in 118,461 individuals from the UK Biobank. Nat Commun 14, 604 (2023). https://doi.org/10.1038/s41467-023-36231-7.
Lamain-De Ruiter M, et al., van Oirschot CM, Vankan-Buitelaar SA, Vonk MA, Wiegers TA, Zwart JJ, Franx A, Moons KG, Koster MP. External validation of prognostic models to predict risk of gestational diabetes mellitus in one Dutch cohort: prospective multicentre cohort study. BMJ. Aug. 30, 2016;354:14338. doi: 10.1136/bmj.i4338. PMID: 27576867.

* cited by examiner

METABOLIC PROFILE SCREENING FOR GESTATIONAL DIABETES

This application claims benefit of U.S. provisional patent application No. 62/714,294, filed Oct. 11, 2019, the entire contents of which are incorporated by reference into this application.

BACKGROUND OF THE INVENTION

Pregnancy induces high blood sugar in about 6-14% of women. This gestational diabetes mellitus (GDM) increases the risk of hypertension and cesarean delivery in the mother, macrosomia and birth trauma in the fetus, metabolic abnormalities in the newborn, and diabetes mellitus, obesity and hypertension in later life. Dietary and lifestyle changes and hypoglycemic agents can significantly reduce adverse outcomes.

Pregnancy increases material insulin resistance, which promotes substrate transfer to the growing fetus. This metabolic perturbation emerges within 14 weeks' gestation (0.37 term) and rises about two-fold by 34 weeks (0.8 term). As a result, insulin sensitivity declines by up to 50%, and insulin secretion by pancreatic β-cells rises up to 250% increase (Kautzky-Willer 1997; Catalano, Tyzbir 1991; Catalano, Huston 1991 Catalano, Huston 1999; 1972). The maximum β-cell secretory response to glucose occurs in the third trimester (Catalano, Tyzbir 1993). About 5-14% of pregnant women have insufficient insulin sensitivity and/or pancreatic β-beta cell reserve for maintaining euglycemia by the fifth or sixth month of gestation (Powe 2016; Ozougwu 2013; Lambie 1926). This GDM approximately doubles the maternal risk of preeclampsia and cesarean delivery (Yovev 2004; Ehrenberg 2004), and confers a major risk for the future development of type 2 diabetes and cardiovascular disorders (Kim 2002; Gunderson 2014; Shostrom 2017). A particular concern is the adverse effects of maternal hyperglycemia on the offspring. These include an increased risk for fetal macrosomia, shoulder dystocia, birth trauma, neonatal hypoglycemia, and epigenetic alterations that predispose in later life to obesity, type 2 DM, metabolic syndrome, and cardiovascular disorders (Boney 2005; Dabelea 2000; Damm 2016; El Hajj 2013, Clausen 2009; Monteiro 2016, Zhao 2016).

Lowering maternal glycemia through diet, exercise, and hypoglycemic agents can reduce the maternal and perinatal morbidity of GDM (Landon 2009; Poolsup 2014). Thus, metabolic control of these gravidas remains an important component of prenatal care. In the United States, GDM screening has evolved from targeting gravidas with risk factors (Wilkerson 1957; Carr 1998) to universal surveillance with the 1-h 50-g oral glucose challenge test (GCT) (Hoet 1954; Moyer 2014; O'Sullivan et al. 1973; Wilkerson 1957; Carr 1998; ACOG). The diagnosis is commonly established by the beginning of the third trimester of pregnancy (0.75 term) with oral glucose tolerance test (GTT). The GCT and GTT have remained central components of prenatal care for more than 50 years, although the specific protocol and diagnostic criteria remain controversial (Carpenter & Coustan 1982; World Health Organization 1998; ADA 2017; IADPSG 2010; Carr 1998). This strategy has major disadvantages for the patient, including the discomfort of venipuncture, inconvenience, time commitment, and late pregnancy diagnosis. Accurate identification in the first trimester of gravidas who will develop GDM would enable therapeutic interventions to normalize maternal metabolic milieu throughout the second and third trimesters. Earlier control of maternal glycemia has the potential to optimize maternal and perinatal outcomes and reduce the offspring risk of type 2 DM and other disorders (McCabe & Pemg, 2017; Brink 2016).

Prior to conception, women who develop GDM demonstrate features of insulin resistance (Catalano et al. 1991) and a higher urinary excretion of putative insulin mediators in the first trimester (Murphy et al. 2016). Before 14 weeks' gestation, various plasma markers are associated with GDM, although have limited value in predicting the onset of the disorder (Correa 2019; Powe 2017; Sacks 2003; Nevalainen 2016; Alunni 2015; Brink 2016; Georgiou 2008; Bao 2015; Ozgu-Erdinc 2015; Rodrigo 2018; Donovan 2018). These studies support the continued search for an indicator detectable in early pregnancy that reliably predicts GDM There remains a need for a maternal metabolic profile in the first trimester that accurately predicts GDM to enable early therapeutic interventions to improve short and long-term health of the mother, fetus, and offspring.

SUMMARY OF THE INVENTION

Described herein are methods, materials, kits, devices, and assays for use in screening, detection, and treatment of diabetes, including diabetes mellitus and gestational diabetes mellitus (GDM). In some embodiments, described is a method of screening for susceptibility to diabetes in a subject. In some embodiments, the method comprises measuring the amount of a plurality of metabolic markers present in a test sample obtained from the subject; comparing the amount of the metabolic markers present in the test sample to reference levels of the markers; and identifying a subject as susceptible to diabetes when the amount of each of the measured markers present in the test sample is increased or decreased relative to the reference levels. In some embodiments, provided is a method of detecting diabetes in a subject. In some embodiments, the method comprises measuring the amount of a plurality of metabolic markers present in a test sample obtained from the subject; comparing the amount of the metabolic markers present in the test sample to reference levels of the markers; and identifying a subject as having diabetes when the amount of each of the measured markers present in the test sample is increased or decreased relative to the reference levels. Also provided is a method of treating diabetes in a subject. In some embodiments, the method comprises measuring the amount of a plurality of metabolic markers present in a test sample obtained from the subject; comparing the amount of the metabolic markers present in the test sample to reference levels of the markers; and treating the subject for diabetes when the amount of each of the measured markers present in the test sample is increased or decreased relative to the reference levels.

In some embodiments of the aforementioned methods, the metabolic marker is dihydroorotate and one or more of: argininate, phenol glucuronide, 7,8-dihydroneopterin, nicotinate ribonucleoside, saccharopine; and lanthionine. In some embodiments, the marker is a combination of a decrease in dihydroorotate, and an increase in argininate, 7,8-dihydroneopterin, and saccharopine. In some embodiments, the marker is a combination of an increase in dihydroorotate, phenol glucuronide, and nicotinate ribonucleoside. In some embodiments, the marker is a combination of an increase in dihydroorotate, phenol glucuronide, nicotinate ribonucleoside, and a decrease in lanthionine. In some embodiments, the plurality of metabolic markers comprises each of dihydroorotate, argininate, phenol glucuronide, 7,8-dihydroneopterin, nicotinate ribonucleoside, saccharopine; and lanthionine. In some embodiments, the identifying of a subject as having diabetes is determined according to the classification tree depicted in FIG. 2. In some embodiments, the reference levels are determined with respect to the values shown in the classification tree of FIG. 2.

In some embodiments, the plurality of metabolic markers comprises each of dihydroorotate, phenol glucuronide, nicotinate ribonucleoside, and saccharopine. In some embodiments, the plurality of metabolic markers comprises an increase in dihydroorotate, phenol glucuronide, and saccharopine; and a decrease in nicotinate ribonucleoside. In some embodiments, the identifying of a subject as having diabetes is determined according to the classification tree depicted in FIG. 4. In some embodiments, the reference levels are determined with respect to the values shown in the classification tree of FIG. 4.

In some embodiments, the metabolic markers further include one or more additional markers selected from the group consisting of: dopamine, octanoylcamitine (c8), 3-methylglutarate/2-methylglutarate, and/or isocitric lactone; and wherein an increase in the additional marker is indicative of diabetes.

In some embodiments of the aforementioned methods, the plurality of metabolic markers comprises 3-hydroxybutyrate, 1,5-anhydroglucitol, homocamosine, and 3-hydroxydodecanedioate. In some embodiments, the marker is a combination of a decrease in 1,5-anhydroglucitol and/or homocamosine, and an increase in 3-hydroxybutyrate, and/or 3-hydroxydodecanedioate. In some embodiments, the plurality of metabolic markers comprises each of 3-hydroxybutyrate, 1,5-anhydroglucitol, homocamosine, and 3-hydroxydodecanedioate. In some embodiments, the identifying of a subject as having diabetes is determined according to the classification tree depicted in FIG. 3. In some embodiments, the reference levels are determined with respect to the values shown in the classification tree of FIG. 3.

In some embodiments, the treating comprises dietary modification including supplements, administration of an oral hypoglycemia agent, or insulin therapy. In some embodiments, the treating comprises diet, exercise, and glycemia surveillance (e.g., frequent testing of blood glucose levels, up to daily monitoring).

In some embodiments, the measuring comprises chromatography or spectrometry. In some embodiments, the chromatography is gas or liquid chromatography. In some embodiments, the spectrometry is mass spectrometry. In some embodiments, the subject is 6-40 weeks pregnant. In some embodiments, the subject is 6-24 weeks pregnant. In some embodiments, the subject is 6-20 weeks pregnant. In some embodiments, the subject is 20-40 weeks pregnant. In some embodiments, the subject is postpartum. In some embodiments, the subject is not pregnant. In some embodiments, the diabetes is diabetes mellitus. In some embodiments, test sample is urine. In some embodiments, the metabolic marker is osmolality normalized. In some embodiments, a classification tree will provide the final algorithm for determining when the markers are increased or decreased for separating diabetes vs normal.

Also described herein is a non-transitory computer-readable medium embodying at least one program that, when executed by a computing device comprising at least one processor, causes the computing device to perform a method described herein. In some embodiments, at least one program contains algorithms, instructions or codes for causing at least one processor to perform the method.

Also described is a non-transitory computer-readable storage medium storing computer-readable algorithms, instructions or codes that, when executed by a computing device comprising at least one processor, cause or instruct the at least one processor to perform the method described herein, or steps within the method.

Additionally described is a computer implemented system. In one embodiment, the system comprises: a sample receiver for receiving a sample provided by an individual; a digital processing device comprising an operating system configured to perform executable instructions and a memory; and a computer program including instructions executable by the digital processing device to provide a treatment to a healthcare provider based on the sample. In some embodiments, the computer program comprises: (i) a metabolite analysis module configured to determine a metabolite level in the sample for at least one metabolite comprising dihydroorotate and one or more of: argininate, phenol glucuronide, 7,8-dihydroneopterin, nicotinate ribonucleoside, saccharopine; and lanthionine, and, any of the metabolites listed in Table 2; (ii) a detection and/or treatment determination module configured to determine the status and/or treatment based on the metabolic marker level; and (iii) a display module configured to provide the status and/or treatment to the healthcare provider.

DETAILED DESCRIPTION OF THE INVENTION

Figure 1:
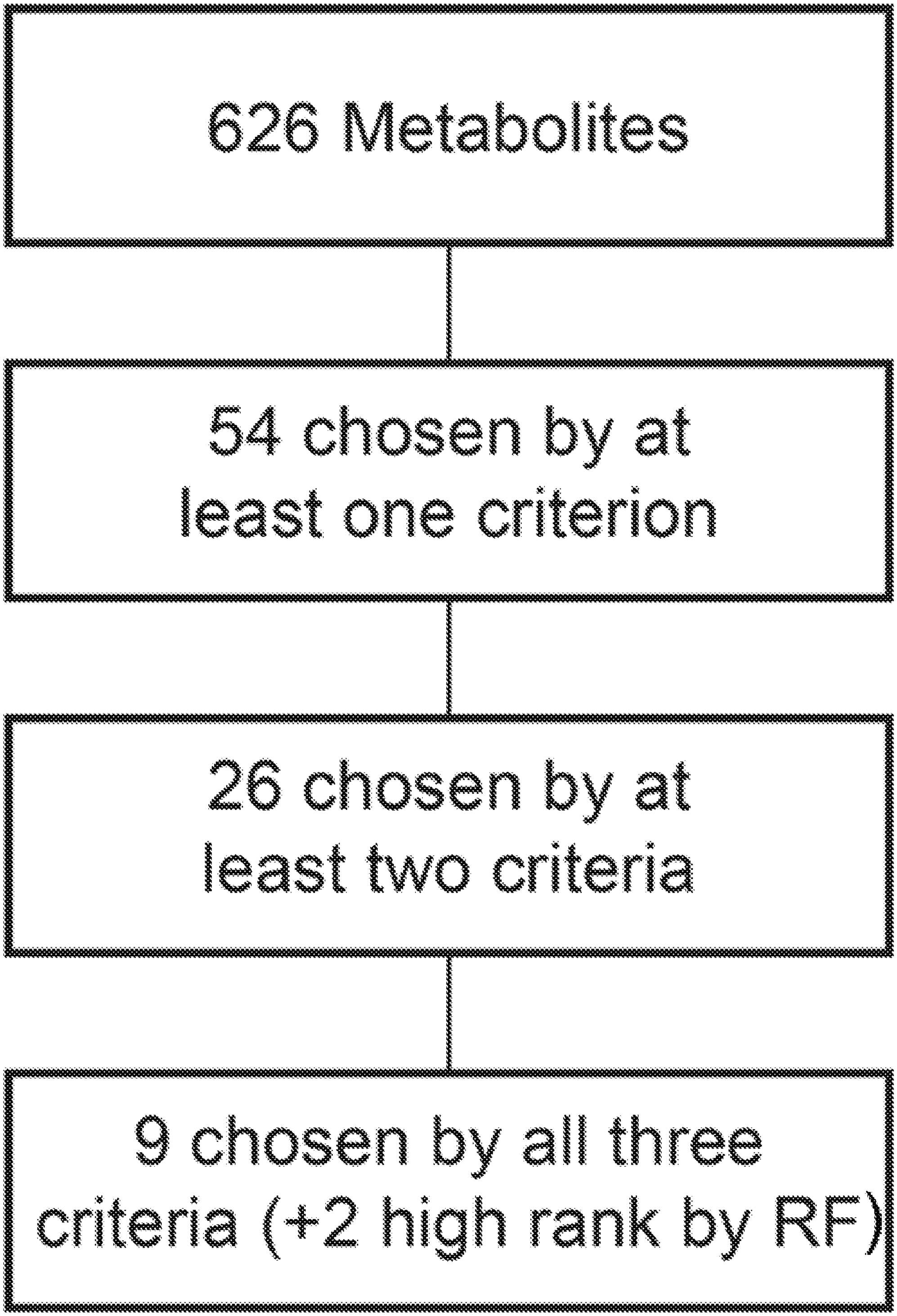
FIG. 1 Consensus metabolite selection. This flow chart depicts the selection process of candidate metabolites that distinguished GDM from CON by random-forest prediction accuracy, random forest GINI worsening, or gradient-boost model. Candidate metabolites for the final model included nine derived from the consensus of all three criteria plus an additional two with very high ranking by random forest.

Disclosed herein is a method for the detection of a metabolic profile of maternal urine that accurately predicts the development of gestational diabetes. This method eliminates the patient burden of the glucose tolerance test and identifies those who will develop gestational diabetes as early as the first trimester. Thus, the implementation of therapeutic interventions can begin in early pregnancy, thereby improving maternal, fetal, and newborn outcomes and reducing the risk of obesity and diabetes mellitus in adolescence and adulthood.

Definitions

All scientific and technical terms used in this application have meanings commonly used in the art unless otherwise specified. As used in this application, the following words or phrases have the meanings specified.

As used herein, a "control" or "reference" sample means a sample that is representative of normal measures of the respective marker, such as would be obtained from normal, healthy control subjects, or a baseline amount of marker to be used for comparison. Typically, a baseline will be a measurement taken from the same subject or patient. The sample can be an actual sample used for testing, or a reference level or range, based on known normal measurements of the corresponding marker. Markers described herein are referred to, interchangeably, as "metabolites" and as "metabolic markers".

As used herein, a "significant difference" means a difference that can be detected in a manner that is considered reliable by one skilled in the art, such as a statistically significant difference, or a difference that is of sufficient magnitude that, under the circumstances, can be detected with a reasonable level of reliability. In one example, an increase or decrease of 10% relative to a reference sample is a significant difference. In other examples, an increase or decrease of 20%, 30%, 40%, or 50% relative to the reference sample is considered a significant difference. In yet another example, an increase of two-fold relative to a reference sample is considered significant.

As used herein, the term "subject" includes any human or non-human animal. The term "non-human animal" includes all vertebrates, e.g., mammals and non-mammals, such as non-human primates, horses, sheep, dogs, cows, pigs, chickens, and other veterinary subjects. In a typical embodiment, the subject is a human.

As used herein, "a" or "an" means at least one, unless clearly indicated otherwise.

As used herein, "predictive accuracy" means the proportion of the observations or subjects that are correctly predicted by the model (random forest, boosting or other model). For example, the proportion of GDM observations that are predicted to be GDM and the proportion of control observations that are predicted to be controls.

As used herein, "GINI criterion" or "GINI index" refers to an alternative measure of accuracy/fit. For a binary outcome such as GDM or control, the GINI criterion measures how homogeneously observations are classified by a model. GINI=1−Pg2−Pc2 where Pg is the proportion of GDM observations classified as GDM and Pc are the proportion of controls classified as controls. The best value is GINI=0 when all GDM observations are classified as GDM (Pg=1 for GDM, Pg=0 for controls) and/or all control observations are classified as controls (Pg=0 for GDM, Pc=1 for controls). The worst GINI value is GINI=0.50 when it is equally likely that a GDM is classified as GDM or control or a control is classified as GDM or control. If omitting a variable (metabolite) as a predictor from a model causes the GINI index to worsen by (for example) 0.40 units, the metabolite is important. If omitting a metabolite only causes the GINI index to worsen by (say) 0.0003 units, it is not an important metabolite by GINI.

As used herein, "random forest model" refers to a multivariable model made up of many classification trees. A random subset of the data and a random subset of the variables (metabolites) are selected and a classification tree is created to predict the (GDM or control) outcome. The data NOT selected to make the tree is called the "out of bag" (OOB) part of the sample for this tree. This process is repeated many times (typically 500 times or more) to create many trees. The final prediction of GBM or control is obtained by a "vote" across all trees. Accuracy is evaluated across the OOB samples.

As used herein, "boosted (logistic) regression" means, for a binary outcome and the simplest form of boosting (ie LogitBoost), all observations are initially given a the same weight of 1/n. A two branch tree (tree "stump"), also called a "weak learner", is generated by splitting on the value of the variable (metabolite) that best distinguishes GDM from control (variable with highest accuracy). The observations are then re-weighted, where observations incorrectly classified by the weak leaner are given higher weight than those correctly classified by the first weak learner. Once the observations are re-weighed, a second weak learner is generated which may use a different variable or the same variable and gives better predictions for the observations with higher weight. This process is repeated, and each new weak learner is added to the previous weak learners. Similar to logistic regression and to trees, the final prediction is therefore a function of a weighed linear function of all the weak learners. The boosting method gives a relative influence value for each metabolite. The influence of a given variable (metabolite) is based on how many times this particular variable is chosen.

As used herein, "consensus variables" means variables (metabolites) chosen as important by more than one model. Examples are illustrated in Example 1 below.

Methods

The invention provides methods for screening, detection, and treatment of diabetes, including diabetes mellitus and gestational diabetes mellitus (GDM). In some embodiments, described is a method of screening for susceptibility to diabetes in a subject. In some embodiments, the method comprises measuring the amount of a plurality of metabolic markers present in a test sample obtained from the subject; comparing the amount of the metabolic markers present in the test sample to reference levels of the markers; and identifying a subject as susceptible to diabetes when the amount of each of the measured markers present in the test sample is increased or decreased relative to the reference levels. In some embodiments, provided is a method of detecting diabetes in a subject. In some embodiments, the method comprises measuring the amount of a plurality of metabolic markers present in a test sample obtained from the subject; comparing the amount of the metabolic markers present in the test sample to reference levels of the markers; and identifying a subject as having diabetes when the amount of each of the measured markers present in the test sample is increased or decreased relative to the reference levels. Also provided is a method of treating diabetes in a subject. In some embodiments, the method comprises measuring the amount of a plurality of metabolic markers present in a test sample obtained from the subject; comparing the amount of the metabolic markers present in the test sample to reference levels of the markers; and treating the subject for diabetes when the amount of each of the measured markers present in the test sample is increased or decreased relative to the reference levels.

In some embodiments of the aforementioned methods, the metabolic marker is dihydroorotate and one or more of: argininate, phenol glucuronide, 7,8-dihydroneopterin, nicotinate ribonucleoside, saccharopine; and lanthionine. In some embodiments, the marker is a combination of a decrease in dihydroorotate, and an increase in argininate, 7,8-dihydroneopterin, and saccharopine. In some embodiments, the marker is a combination of an increase in dihydroorotate, phenol glucuronide, and nicotinate ribonucleoside. In some embodiments, the marker is a combination of an increase in dihydroorotate, phenol glucuronide, nicotinate ribonucleoside, and a decrease in lanthionine. In some embodiments, the plurality of metabolic markers comprises each of dihydroorotate, argininate, phenol glucuronide, 7,8-dihydroneopterin, nicotinate ribonucleoside, saccharopine; and lanthionine. In some embodiments, the identifying of a subject as having diabetes is determined according to the classification tree depicted in FIG. 2. In some embodiments, the reference levels are those shown in the classification tree of FIG. 2. In some embodiments, the metabolic markers further include one or more additional markers selected from the group consisting of: dopamine, octanoylcamitine (c8), 3-methylglutarate/2-methylglutarate, and/or isocitric lactone; and wherein an increase in the additional marker is indicative of diabetes.

In a representative example, the comparing of the amount of the metabolic markers present in the test sample to reference levels of the markers using the classification tree depicted in FIG. 2 proceeds as follows. The sample, e.g., a urine sample obtained from the subject, is assayed for dihydroorotate. If the measured level of dihydroorotate is below the reference value of 0.24 (osmolality normalized), the sample is assayed for argininate. If the measured level of argininate is greater than the reference level of 0.79, the sample is assayed for 7,8-dihydroneopterin. If the measured level of 7,8-dihydroneopterin is greater than the reference level of 0.45, the sample is assayed for saccharopine. If the measured level of saccharopine is greater than the reference level of 1.2, the subject is identified as a subject in need of treatment for diabetes mellitus. Further examples of this progression of the analysis are described below.

In some embodiments, the plurality of metabolic markers comprises each of dihydroorotate, phenol glucuronide, nicotinate ribonucleoside, and saccharopine. In some embodiments, the plurality of metabolic markers comprises an increase in dihydroorotate, phenol glucuronide, and saccharopine; and a decrease in nicotinate ribonucleoside. In some embodiments, the identifying of a subject as having diabetes is determined according to the classification tree depicted in FIG. 4 (see Example 4 below). In some embodiments, the reference levels are those shown in the classification tree of FIG. 4.

In some embodiments of the aforementioned methods, the plurality of metabolic markers comprises 3-hydroxybutyrate, 1,5-anhydroglucitol, homocamosine, and 3-hydroxydodecanedioate. In some embodiments, the marker is a combination of a decrease in 1,5-anhydroglucitol and/or homocamosine, and an increase in 3-hydroxybutyrate, and/or 3-hydroxydodecanedioate. In some embodiments, the plurality of metabolic markers comprises each of 3-hydroxybutyrate, 1,5-anhydroglucitol, homocamosine, and 3-hydroxydodecanedioate. In some embodiments, the identifying of a subject as having diabetes is determined according to the classification tree depicted in FIG. 3. In some embodiments, the reference levels are those shown in the classification tree of FIG. 3.

In some embodiments, the treating comprises glycemia surveillance (frequent, up to daily measurement of material glucose levels), dietary alterations, antioxidant supplements, exercise, and/or the administration of an oral hypoglycemia agent or insulin therapy. Dietary antioxidants can bolster material/fetal mitochondrial function, which can ameliorate the metabolic milieu and potentially reduce the need for hypoglycemic agents. Such intervention in the first-trimester can reduce fetal and maternal morbidity and lower the risk of significant medical disorders in adult offspring.

In some embodiments, the measuring comprises chromatography or spectrometry. In some embodiments, the chromatography is gas or liquid chromatography. In some embodiments, the spectrometry is mass spectrometry. In some embodiments, the subject is 6-40 weeks pregnant. In some embodiments, the subject is 6-24 weeks pregnant. In some embodiments, the subject is 6-20 weeks pregnant. In some embodiments, the subject is 20-40 weeks pregnant. In some embodiments, the subject is postpartum. In some embodiments, the diabetes is diabetes mellitus. In some embodiments, test sample is urine. In some embodiments, the metabolic marker is osmolality normalized. In some embodiments, a classification tree of metabolites identified by multivariate methods will provide the algorithm for determining when the markers are increased or decreased.

Figure 2:
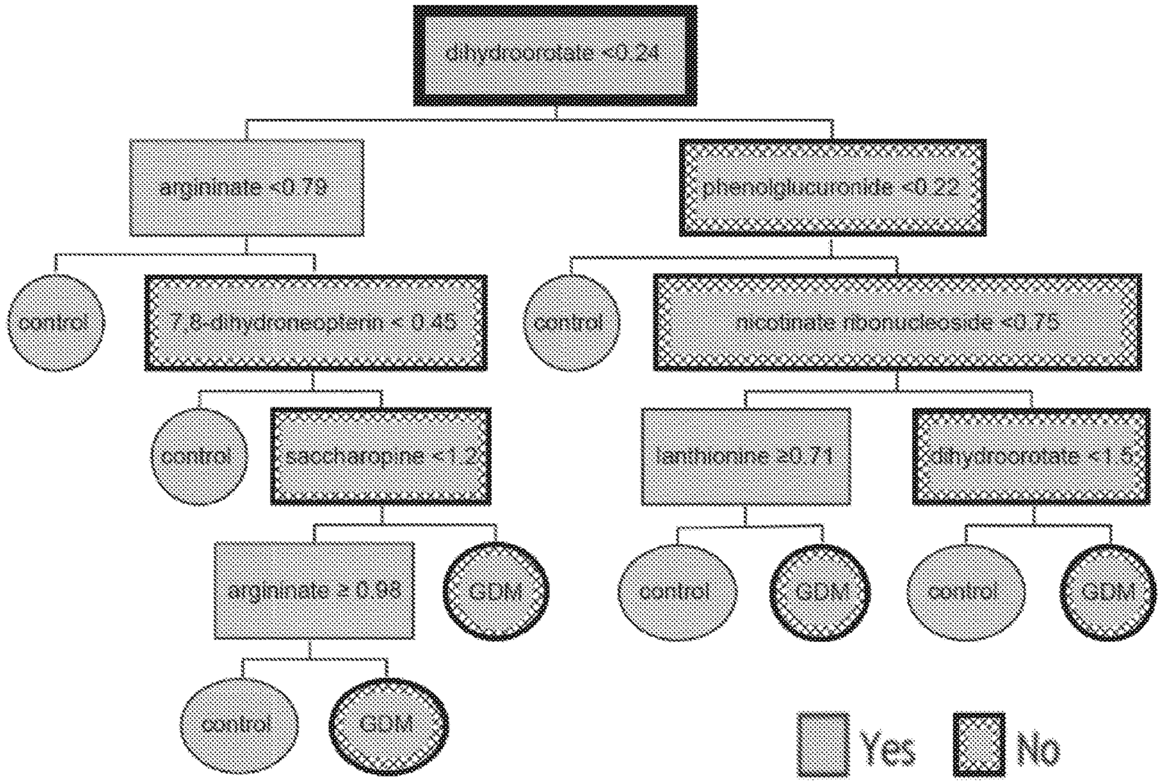
FIG. 2 Final Classification tree model. This shows the classification tree analysis of the seven metabolites with the best separation of GDM versus CON. The green color indicates a node where the majority and the prediction is control. The gold color indicates a node where the majority and prediction is GDM. For a given condition at a tree node, such as "argininate <0.79", one traverses the tree to the left if the condition is true ("yes") and one traverses the tree to the right if the condition is false ("no"). The number displayed at each node represents the metabolite level scaled to the respective median and referenced to osmolality in the original scale. illustrates a classification tree that can guide implementation of one embodiment of the method using osmolality normalized urine metabolite measurements from a subject to determine diabetic status.

In some embodiments, a sample of urine obtained from a subject is assayed for the levels of the seven metabolic markers identified in FIG. 2 (top seven metabolites of Table 2). Typically the subject is between 6 and 20 weeks pregnant. In some embodiments, the subject is greater than 20 weeks pregnant. The measured amounts are normalized to urine osmolality. In some embodiments, the analysis begins with the first level shown in the classification tree depicted in FIG. 2, dihydroorotate. If the level of dihydroorotate is below the reference level for dihydroorotate (e.g., 0.24 osmolality normalized units), the analysis moves to argininate, following the left side of the classification tree. If argininate is below the reference level for this marker, then the subject does not have gestational diabetes mellitus. If argininate is above the reference level, then the analysis moves to 7,8-dihydroneopterin. If 7,8-dihydroneopterin is below its reference level (e.g., 0.45), then the subject does not have GDM. If 7,8-dihydroneopterin is above its reference level, then the analysis moves to saccharopine. Sacchoropine below its reference level (1.2), combined with argininate at or above 0.98, is indicative of a subject who does not have GDM. Saccharopine above its reference level (combined with dihydroorotate, argininate and 7,8-dihydroneopterin above their reference levels) is indicative of GDM.

If dihydroorotate is above the reference level (0.24), then the analysis moves to phenol glucuronide. If phenol glucuronide is below its reference level (e.g., 0.22), the subject does not have GDM. If phenol glucuronide is above its reference level, then the analysis moves to nicotinate ribonucleoside. If nicotinate ribonucleoside is below its reference level (0.75), and lanthionine is at or above its reference level (0.71), the subject does not have GDM. If nicotinate ribonucleoside is below its reference level and lanthionine is below its reference level, the subject has GDM. If nicotinate ribonucleoside is above its reference level, but dihydroorotate is below 1.5, the subject does not have GDM. If nicotinate ribonucleoside is above its reference level and dihydroorotate is above 1.5, then the subject has GDM.

For use in the methods described herein, representative examples of the sample include, but are not limited to, blood, plasma or serum, saliva, urine, cerebral spinal fluid, milk, cervical secretions, semen, tissue, cell cultures, and other bodily fluids or tissue specimens. In some embodiments, the sample is urine.

Methods of measuring metabolites include, but are not limited to, nuclear magnetic resonance (NMR) spectroscopy, high performance liquid chromatography (HPLC), gas chromatography, thin layer chromatography, electrochemical analysis, mass spectroscopy, refractive index spectroscopy, ultra-violet spectroscopy, fluorescent analysis, radiochemical analysis, near-infrared spectroscopy, gas chromatography, and light scattering analysis. In some embodiments, the measuring comprises gas or liquid chromatography. In some embodiments, the measuring comprises mass spectrometry.

Kits and Assay Standards

The invention provides kits comprising a set of reagents suitable for use in the methods described herein, and optionally, one or more suitable containers containing reagents of the invention. Reagents include molecules that specifically bind and/or amplify and/or detect one or more markers of the invention. Such molecules can be provided in the form of a microarray or other article of manufacture for use in an assay described herein.

Kits of the invention optionally comprise an assay standard or a set of assay standards, either separately or together with other reagents. An assay standard can serve as a normal control by providing a reference level of normal expression for a given marker that is representative of a healthy individual.

Devices

The invention provides a device suitable for use in the methods described herein. A device is capable of detecting and measuring one or more metabolic markers of the invention. The device optionally comprises a processor programmed to perform an analysis of the measurements of metabolic markers according to the methods described herein. In some embodiments, the analysis includes implementation of the classification tree depicted in FIG. 2. In some embodiments, the analysis includes implementation of the classification tree depicted in FIG. 3. In some embodiments, the analysis includes implementation of the classification tree depicted in FIG. 4.

Computer Implementations

Provided herein, in certain aspects, are computer implemented systems for use in methods herein, such as methods of screening, methods of detecting, methods of treatment, methods of metabolic profiling, and methods of recommending a treatment. In some embodiments, computer implemented systems herein comprise: (a) a sample receiver for receiving a sample provided by an individual; (b) a digital processing device comprising an operating system configured to perform executable instructions and a memory; and (c) a computer program including instructions executable by the digital processing device to provide a treatment to a healthcare provider based on the sample. In some embodiments, the computer program comprises: (i) a metabolite analysis module configured to determine a metabolite level in the sample for at least one metabolite comprising argininate, phenol glucuronide, 7,8-dihydroneopterin, nicotinate ribonucleoside, saccharopine; and lanthionine, and, any combination of the metabolites listed in Table 2; (ii) a treatment determination module configured to determine the treatment based on the metabolite expression level relative to a reference level; and (iii) a display module configured to provide the result and/or treatment to the healthcare provider.

The invention provides a non-transitory computer-readable medium encoded with computer-executable instructions for performing the methods described herein. In another embodiment, the invention provides a non-transitory computer-readable medium embodying at least one program that, when executed by a computing device comprising at least one processor, causes the computing device to perform one or more of the methods described herein. In some embodiments, the at least one program contains algorithms, instructions or codes for causing the at least one processor to perform the method(s). Likewise, the invention provides a non-transitory computer-readable storage medium storing computer-readable algorithms, instructions or codes that, when executed by a computing device comprising at least one processor, cause or instruct the at least one processor to perform a method described herein.

Those of ordinary skill in the art would understand that the various embodiments of the method described herein, including analysis of metabolic profiles, classification tree, and determination of GDM status, for example, can be implemented in electronic hardware, computer software, or a combination of both (e.g., firmware). Whether the present method is implemented in hardware and/or software may depend on, e.g., the particular application and design constraints imposed on the overall system. Ordinary artisans can implement the present method in varying ways depending on, e.g., particular application and design constraints, but such implementation decisions do not depart from the scope of the present disclosure.

The computer programs/algorithms for performing the present method can be implemented with, e.g., a general-purpose processor, a digital signal processor (DSP), an application-specific integrated circuit (ASIC), a field-programmable gate array (FPGA), or other programmable logic device, discrete gate or transistor logic, discrete hardware components, or any combination thereof designed to perform the functions and steps described herein. A general-purpose processor can be a microprocessor, but alternatively the processor can be any conventional processor, controller, microcontroller or state machine. A processor can also be implemented as a combination of computing devices, e.g., a combination of a DSP and a microprocessor, a plurality of microprocessors, one or more microprocessors in conjunction with a DSP core, or any other such configuration.

The steps of the present method, or the computer programs/algorithms for performing the method, can be embodied directly in hardware, in a software module executed by a processor, or in a combination of hardware and software (e.g., firmware). A software module can reside in, e.g., RAM memory, flash memory, ROM memory, EPROM memory, EEPROM memory, registers, a hard drive, a solid-state drive, a removable disk or disc, a CD-ROM, or any other form of storage medium known in the art. An exemplary storage medium is coupled to the processor such that the processor can read information from, and write information to, the storage medium. Alternatively, the storage medium can be integral to the processor. The processor and the storage medium can reside in, e.g., an ASIC, which in turn can reside in, e.g., a user terminal. In the alternative, the processor and the storage medium can reside as discrete components in, e.g., a user terminal.

In one or more exemplary designs, the functions for carrying out the method described herein can be implemented in hardware, software, firmware or any combination thereof. If implemented in software, the functions can be stored on or transmitted over a computer-readable medium as instructions or codes. Computer-readable media include without limitation computer storage media and communication media, including any medium that facilitates transfer of a computer program/algorithm from one place to another. A storage medium can be any available medium that can be accessed by a general-purpose or special-purpose computer or processor. As a non-limiting example, computer-readable media can comprise RAM, ROM, EEPROM, CD-ROM or other optical disc storage, magnetic disk storage or other magnetic storage devices, or any other medium that can be used to carry or store a computer program/algorithm in the form of instructions/codes and/or data structures and that can be accessed by a general-purpose or special-purpose computer or processor. In addition, any connection is deemed a computer-readable medium. For example, if the software is transmitted from a website, a server or other remote source using a coaxial cable, fiber optic cable, twisted pair, digital subscriber line (DSL), or a wireless technology such as infrared, radio wave or microwave, then the coaxial cable, fiber optic cable, twisted pair, DSL, or wireless technology such as infrared, radio wave or microwave are computer-readable media. Discs and disks include without limitation compact disc (CD), laser disc, optical disc, digital versatile disc (DVD), blu-ray disc, hard disk and floppy disk, where discs normally reproduce data optically using a laser, while disks normally reproduce data magnetically. Combinations of the above are also included within the scope of computer-readable media.

The methods described herein can be automated. Accordingly, in some embodiments the method is implemented with a computer system (e.g., a server, a desktop computer, a laptop, a tablet or a smartphone) comprising at least one processor. The computer system can be configured or provided with algorithms, instructions or codes for performing the method which are executable by the at least one processor. The computer system can generate a report containing information on any or all aspects relating to the method, including results of the analysis of the biological sample from the subject. The disclosure further provides a non-transitory computer-readable medium encoded with computer-executable instructions for performing the present method.

Example Embodiments

Example embodiment 1 is a method of screening for susceptibility to diabetes in a subject, the method comprising: (a) measuring the amount of a plurality of metabolic markers present in a test sample obtained from the subject; (b) comparing the amount of the metabolic markers present in the test sample to reference levels of the markers; (c) identifying a subject as susceptible to diabetes when the amount of each of the measured markers present in the test sample is increased or decreased relative to the reference levels; wherein the plurality of metabolic markers comprises dihydroorotate and one or more of argininate, phenol glucuronide, 7,8-dihydroneopterin, nicotinate ribonucleoside, saccharopine; and lanthionine.

Embodiment 2 is a method of detecting diabetes in a subject, the method comprising: (a) measuring the amount of a plurality of metabolic markers present in a test sample obtained from the subject; (b) comparing the amount of the metabolic markers present in the test sample to reference levels of the markers; (c) identifying a subject as having diabetes when the amount of each of the measured markers present in the test sample is increased or decreased relative to the reference levels; wherein the metabolic markers comprise dihydroorotate and one or more of: argininate, phenol glucuronide, 7,8-dihydroneopterin, nicotinate ribonucleoside, saccharopine; and lanthionine.

Embodiment 3 is a method of treating diabetes in a subject, the method comprising: (a) measuring the amount of a plurality of metabolic markers present in a test sample obtained from the subject; (b) comparing the amount of the metabolic markers present in the test sample to reference levels of the markers; (c) treating the subject for diabetes when the amount of each of the measured markers present in the test sample is increased or decreased relative to the reference levels; wherein the metabolic markers comprise dihydroorotate and one or more of argininate, phenol glucuronide, 7,8-dihydroneopterin, nicotinate ribonucleoside, saccharopine; and lanthionine.

Embodiment 4: The method of any of the preceding embodiments, wherein the marker is a combination of a decrease in dihydroorotate, and an increase in argininate, 7,8-dihydroneopterin, and saccharopine.

Embodiment 5: The method of any of the preceding embodiments, wherein the marker is a combination of an increase in dihydroorotate, phenol glucuronide, and nicotinate ribonucleoside.

Embodiment 6: The method of any of the preceding embodiments, wherein the marker is a combination of an increase in dihydroorotate, phenol glucuronide, nicotinate ribonucleoside, and a decrease in lanthionine.

Embodiment 7: The method of embodiment 4, wherein the plurality of metabolic markers comprises each of dihydroorotate, argininate, phenol glucuronide, 7,8-dihydroneopterin, nicotinate ribonucleoside, saccharopine; and lanthionine.

Embodiment 8: The method any of the preceding embodiments, wherein the identifying of a subject as having diabetes is determined according to the classification tree depicted in FIG. 2.

Embodiment 9: The method of embodiment 8, wherein the reference levels are those shown in the classification tree of FIG. 2.

Embodiment 10: The method of any of embodiments 4 to 9, wherein the metabolic markers further include one or more additional markers selected from the group consisting of: dopamine, octanoylcamitine (c8), 3-methylglutarate/2-methylglutarate, and/or isocitric lactone; and wherein an increase in the additional marker is indicative of diabetes.

Embodiment 11: The method of embodiment 3, wherein the treating comprises dietary modification, administration of an oral hypoglycemia agent, or insulin therapy.

Embodiment 12: The method of any of the preceding embodiments, wherein the measuring comprises chromatography or spectrometry.

Embodiment 13: The method of embodiment 12, wherein the chromatography is gas or liquid chromatography.

Embodiment 14: The method of embodiment 12, wherein the spectrometry is mass spectrometry.

Embodiment 15: The method of any one of embodiments 1 to 14, wherein the subject is 6-40 weeks pregnant.

Embodiment 16: The method of any one of embodiments 1 to 14, wherein the subject is postpartum.

Embodiment 17: The method of any of the preceding embodiments wherein the diabetes is diabetes mellitus.

Embodiment 18: The method of any of the preceding embodiments wherein test sample is urine.

Embodiment 19: The method of embodiment 18, wherein the metabolic marker is osmolality normalized.

Embodiment 20: The method of any of the preceding embodiments, wherein multivariate statistical analysis and/or a mathematical method is used to determine when the markers are increased or decreased.

Embodiment 21 is a method of screening for susceptibility to diabetes in a subject, the method comprising: (a) measuring the amount of a plurality of metabolic markers present in a test sample obtained from the subject; (b) comparing the amount of the metabolic markers present in the test sample to reference levels of the markers; (c) identifying a subject as susceptible to diabetes when the amount of each of the measured markers present in the test sample is increased or decreased relative to the reference levels; wherein the plurality of metabolic markers comprises 3-hydroxybutyrate, 1,5-anhydroglucitol, homocamosine, and 3-hydroxydodecanedioate.

Embodiment 22 is a method of detecting diabetes in a subject, the method comprising: (a) measuring the amount of a plurality of metabolic markers present in a test sample obtained from the subject; (b) comparing the amount of the metabolic markers present in the test sample to reference levels of the markers; (c) identifying a subject as having diabetes when the amount of each of the measured markers present in the test sample is increased or decreased relative to the reference levels; wherein the metabolic markers comprise 3-hydroxybutyrate, 1,5-anhydroglucitol, homocamosine, and 3-hydroxydodecanedioate.

Embodiment 23 is a method of treating diabetes in a subject, the method comprising: (a) measuring the amount of a plurality of metabolic markers present in a test sample obtained from the subject; (b) comparing the amount of the metabolic markers present in the test sample to reference levels of the markers; (c) treating the subject for diabetes when the amount of each of the measured markers present in the test sample is increased or decreased relative to the reference levels; wherein the plurality of metabolic markers comprises 3-hydroxybutyrate, 1,5-anhydroglucitol, homocamosine, and 3-hydroxydodecanedioate.

Embodiment 24: The method of any of embodiments 21 to 23, wherein the marker is a combination of a decrease in 1,5-anhydroglucitol and/or homocarnosine, and an increase in 3-hydroxybutyrate, and/or 3-hydroxydodecanedioate.

Embodiment 25: The method of embodiment 24, wherein the plurality of metabolic markers comprises each of 3-hydroxybutyrate, 1,5-anhydroglucitol, homocarnosine, and 3-hydroxydodecanedioate.

Embodiment 26: The method any of the preceding embodiments, wherein the identifying of a subject as having diabetes is determined according to the classification tree depicted in FIG. 3.

Embodiment 27: The method of embodiment 26, wherein the reference levels are those shown in the classification tree of FIG. 3.

Embodiment 28: The method of embodiment 23, wherein the treating comprises dietary modification, administration of an oral hypoglycemia agent, or insulin therapy.

Embodiment 29: The method of any of embodiments 21 to 28, wherein the measuring comprises chromatography or spectrometry.

Embodiment 30: The method of embodiment 29, wherein the chromatography is gas or liquid chromatography.

Embodiment 31: The method of embodiment 29, wherein the spectrometry is mass spectrometry.

Embodiment 32: The method of embodiment 21, wherein the subject is 6-40 weeks pregnant.

Embodiment 33: The method of embodiment 21, wherein the subject is postpartum.

Embodiment 34: The method of any of embodiments 21 to 33, wherein the diabetes is diabetes mellitus.

Embodiment 35: The method of any of embodiments 21 to 34, wherein test sample is urine.

Embodiment 36: The method of embodiment 35, wherein the metabolic marker is osmolality normalized.

Embodiment 37: The method of any of embodiments 21 to 36, wherein multivariate statistical analysis and/or a mathematical method is used to determine when the markers are increased or decreased.

Embodiment 38 is a non-transitory computer-readable medium embodying at least one program that, when executed by a computing device comprising at least one processor, causes the computing device to perform the method of any one of embodiments 1-37.

Embodiment 39: The medium of embodiment 38, wherein the at least one program contains algorithms, instructions or codes for causing the at least one processor to perform the method.

Embodiment 40 is a non-transitory computer-readable storage medium storing computer-readable algorithms, instructions or codes that, when executed by a computing device comprising at least one processor, cause or instruct the at least one processor to perform the method of any one of embodiments 1-39.

Examples

The following examples are presented to illustrate the present invention and to assist one of ordinary skill in making and using the same. The examples are not intended in any way to otherwise limit the scope of the invention.

Example 1: Early Pregnancy Metabolites Predict Gestational Diabetes Mellitus This Example demonstrates that a material metabolic profile as early as the first prenatal visit can accurately identify GDM. Advanced analytical methods were used to generate a urinary metabolite model that accurately predicted gestational diabetes (GDM) in early pregnancy. A model comprising seven early-pregnancy urinary metabolites predicted GDM with high accuracy (96.7%). The accuracy of the model was independent of maternal age, body mass index, and time of urine collection. This Example reports the first proof of the concept that an algorithm utilizing a metabolic profile in early pregnancy can accurately identify GDM.

A major pregnancy adaptation is insulin resistance, which emerges by 14 weeks' gestation (0.37 term) and rises up to two-fold by late pregnancy.[1] About 5-12% of pregnant women in North America have insufficient insulin sensitivity and/or pancreatic β-cell reserve for maintaining euglycemia.[2] This gestational diabetes (GDM) increases the short-term morbidity risk for the mother (preeclampsia, cesarean delivery) and fetus (macrosomia, birth trauma). For over 60 years, glucose challenge/tolerance tests have been the diagnostic standard for GDM, usually performed in late pregnancy.[3] While normalizing maternal glycemia can diminish short-term morbidity,[4] this burdensome diagnostic approach has considerable disadvantages, including time involvement and delaying therapy until the last quarter of gestation.

A further rationale for treating GDM in early pregnancy is the growing evidence that gestational diabetes via adverse intrauterine programming predisposes the fetus in later life to obesity, type 2 diabetes, and cardiovascular disease.[5,6,7,8,9,10,11,12,13,14,15] Normalizing the maternal metabolic milieu in early pregnancy may diminish the oxidative stress and inflammation that putatively impair insulin sensitivity and pancreatic β-cell function, which predispose the mother and child to disabling medical disorders.[5,6,7] With an accuracy <80%, first-trimester biomarkers have lacked sufficient sensitivity and specificity for GDM diagnosis.[16,17,18,19,20] The objective of this metabolomics study was to determine whether a large, diverse array of metabolites and advanced statistical methods could identify a urinary metabolic profile that accurately predicts GDM in early pregnancy. Such a discovery would enable 1) noninvasive diagnosis of GDM before 14 weeks of gestation and 2) future studies to determine to what extent early therapeutic interventions reduce perinatal morbidity and the transgenerational transmission of obesity, type 2 diabetes and cardiovascular disease.

Materials and Methods

A nested, observational case-control study determined the metabolic profile of urine from normal singleton gravidas [control (CON)] versus those who developed GDM by glucose challenge (GCT)/tolerance tests (GTT).[3] The GTC results were considered diagnostic for plasma glucose levels 2200 mg/dl, or a little lower for some patients with risk factors. Fasting glucose level of >95 mg/dl (for GCT intolerant) or a first-trimester $HbA_1c$ (≥5.7%) were also used to identify GDM. GDM were paired to CON subjects by age, pre-pregnancy body mass index (BMI), and gestational age at urine collection. A repository of the Global Alliance to Prevent Prematurity and Stillbirth (Seattle, WA) supplied the de-identified urine samples. All participating gravidas signed written, informed consent forms under protocols approved by the institutional review board of the University of Washington Medical Center, Swedish Medical Center Seattle, Yakima Valley Memorial Hospital, and Seattle Children's Hospital.

Random urine specimens were collected at 6-19 weeks of gestation and stored at −80° C. until analysis by Metabolon, Inc. (Durham, NC). Urine samples were analyzed for 951 diverse, low-molecular weight (<1000) biochemicals by ultra-performance liquid chromatography/mass spectrometry-tandem mass spectroscopy (UPLC-MS/MS) with positive ion mode electrospray ionization, UPLC-MS/MS with negative ion mode electrospray ionization, and gas chromatography/mass spectrometry.[21] The platform identified metabolites by comparison to mass spectra from purified standards. The total process variability was 10%. Quality control samples provided process control. Peak areas for each metabolite were scaled to the median value and osmolality to adjust for fluid intake.

Bivariate Analysis. The p values for comparing continuous variables that follow the normal distribution were computed with t tests. The p values for non-time dependent continuous variables that did not follow the normal distribution on any scale were computed using the Wilcoxon rank sum test. The p values for comparing categorical variables such as race/ethnicity were computed using the exact permutation chi-square test or Fisher's exact test. Means±SE were reported. Differences were significant at $p<0.05$.

The statistical analysis of metabolites excluded xenobiotics and partially characterized compounds. The remaining subset of 626 endogenous compounds comprised peptides, amino acids, carbohydrates, fatty acids, nucleotides, enzyme cofactors, and vitamins. Metabolite means were compared on the log scale between GDM versus CON, and log scale data were summarized with means and standard errors (SE). Differences were nominally significant at $p<0.05$. The effect size of the difference was denoted as the mean difference (GDM−CON, log scale) expressed in standard deviation (SD) units.

Multivariate Analysis. Random forest predictive accuracy, random forest GINI worsening, and gradient boosted logistic regression (gradient boost model) were used for multivariate analysis. Consensus ranking of the top metabolites by two or more of these three criteria were used to select compounds simultaneously associated with GDM versus CON. A smaller biochemical subset considered for the final predictive model was selected by a consensus ranking of the top metabolites by all three criteria, or the most important metabolite identified by a given method.

Using the identified compounds, a classification tree derived the final predictive algorithm. Sensitivity, specificity, accuracy (unweighted mean of sensitivity and specificity), and the receiver operating characteristic (ROC) area were reported for the final model. Computations were carried out using SAS version 9.4 (SAS Inc, Cary, NC) and R version 3.5.2 for random forest and gradient-boost model (R Project for Statistical Computing, www.r-project.org).

Results

About two-thirds of the 46 GDM were diagnosed in the third trimester with remainder distributed almost equally between the first and second trimesters (Table 1). A GCT level of ≥200 mg/dl or a GTT (Z two criteria in all but one case with one criterion) was used to identify 60.9% of cases. GCT value of 180±1.4 mg/dl (range: 171-187 mg/dl) was used to select 32.6%. A negligible number were selected by fasting glucose (GCT intolerant) or a first-trimester $HbA_1c$. Of the 46 GDM, maternal glycemia was managed by diet in 23 (50.0%), oral hypoglycemic agents in 19 (41.3%), and insulin in 4 (8.7%). Of the cases diagnosed by a lower OCT threshold (>170 mg/dl), six (40%) were managed by diet, and nine (60%) were treated with oral agents. The one case identified by fasting glucose and the two by $HbA_1$ required insulin and oral agents, respectively. In the CON group, the GTC gestational age was 27±0.7 weeks (p=0.067 versus GDM); and the one-hour plasma glucose level was 108±2.9 mg/dl ($p<0.0001$ versus GDM).

TABLE 1

Gestational age and GCT glucose by method of GDM diagnosis

| GDM Diagnosis | <12 weeks | 12-23 weeks | >24 weeks | |
|---|---|---|---|---|
| N (%) | 8 (17.4) | 7 (15.2) | 31 (67.4) | |
| GA (wks) | 9.7 ± 0.5 | 17.0 ± 1.4 | 27.2 ± 0.3 | |
| GTC Glucose (mg/dl) | 150 ± 6.9 | 180 ± 7.6 | 180 ± 5.7 | |
| Diagnosis (n) | | | | Total (%) |
| GTT | 4 | 1 | 17 | 22 (47.8) |
| GCT (≥200 mg/dl) | 0 | 1 | 5 | 6 (13.0) |
| GCT (171-187 mg/dl)* | 1 | 6 | 8 | 15 (32.6) |
| Fasting (>95 ml/dl) 0 | 0 | 1 | 0 | 1 (2.2) |
| $HbA_1c$ (≥5.7%) | 2 | 0 | 0 | 2 (4.3) |

*with risk factors; N, number; GA, gestational age

GDM-CON pairs were well matched for maternal age (GDM: 32.2±0.7 years; CON: 31.8±0.6 years; p=0.56), BMI (GDM: 31.5±1.0 kg/m$^2$; CON: 30.0 t 1.0 kg/m$^2$; p=0.18), and gestational age at urine collection (GDM: 11.7±0.4 weeks; CON: 12.0±0.4 weeks; p=0.46). No significant differences occurred for the unmatched parity (GDM: 2.5 t 0.3, CON: 1.9±0.3; p=0.31) and race/ethnicity (white: GDM 27, CON 37; Hispanic: GDM: 9, CON 2; Asian: GDM 5, CON 2; mixed: GDM 5, CON 5; p=0.063). Scree plots of the random forest accuracy, random forest GINI, or the gradient-boost model (relative importance) values versus metabolite ranking showed a leveling off ("break point") after no more than 30 metabolites of highest rank. Of the 626 metabolites 54 were among the top 30 by at least one of the three criteria distinguishing independently GDM from CON, and 26 of 54 compounds had a high rank by at least two criteria (FIG. 1). Nine compounds were identified as important by all three criteria (FIG. 1, Table 2). The final 11 model candidates included two additional metabolites with a very high rank by random forest (Table 3). In GDM, six of the 11 metabolites differed significantly (nominal p<0.05) from CON as revealed by effect size. PGP-22T1

TABLE 2

Candidate urinary metabolites identified by three multivariate criteria for separating GDM versus CON (bold type) or by a very high rank by random forest (normal type).

| Metabolite | Functional Pathway | Effect Size* |
|---|---|---|
| **argininate**† | arginine catabolism | 0.733** |
| **saccharopine**† | lysine catabolism | 0.646** |
| **dihydroorotate**† | pyrimidine synthesis | 0.558 |
| **dopamine** | tyrosine metabolism | 0.254 |
| **isocitrate lactone** | tricarboxylic acid cycle | 0.408 |
| octanoylcarnitine | fatty acid oxidation | 0.124 |
| **3-methylglutarate/ 2-methylglutarate** | fatty acid oxidation | 0.108 |
| **lanthionine**† | anti-oxidation anti-inflammation | −0.509 |
| **nicotinate ribonucleoside**† | anti-oxidation anti-inflammation bioenergetics | 0.655** |
| **7,8-dihydroneopterin**† | anti-oxidation | 0.464** |
| phenol glucuronide† | phenol metabolism (gut microbiota) | 0.596** |

*(GDM-CON)SD, log scale;
**nominal p < 0.05;
†seven metabolites selected for the final predictive model

TABLE 3

Predictive accuracy in early pregnancy for GDM according to the classification tree level.

| Level | Metabolites | Sensitivity (%) | Specificity (%) | Accuracy (%) | ROC Area |
|---|---|---|---|---|---|
| 1 | di | 78.3 | 65.2 | 71.7 | 0.717 |
| 2 | di ar pg | 78.3 | 78.3 | 78.3 | 0.832 |
| 3 | di ar pg ne nr | 89.1 | 73.9 | 81.5 | 0.906 |
| 4 | di ar pg ne nr sa la | 89.1 | 91.3 | 90.2 | 0.946 |
| 5 | di ar pg ne nr sa la | 97.8 | 95.7 | 96.7 | 0.993 |

Di, dihydroorotate; ar, argininate; pg, phenylglucuronide; ne, 7,8-dihydroneopterin; nr, nicotinate ribonucleoside; sa, saccharopine; la, lanthionine In the final classification tree model (FIG. 2), seven of the 11 metabolites simultaneously predicted gestational diabetes with a high degree of accuracy. The nominal prediction accuracy of the model increased according to the number of tree levels (Table 3). The accuracy rose progressively from 71.7% for a one-level tree utilizing a single metabolite to 96.7% for the final tree incorporating all seven metabolites. The final tree had a nominal sensitivity of 97.8% (45/46), a specificity of 95.7% (44/46), and a ROC area 0.993.

Principal Findings. The high predictive accuracy (96.7%) of the model provides proof of the concept that advanced statistical analysis of a large, diverse panel of urinary biochemicals in early pregnancy can identify a metabolite profile highly selective for GDM. Moreover, the high accuracy was independent of maternal age, BMI, and time of urine collection—all of which facilitate clinical use.

Results. The 11 metabolites distinguishing GDM in early pregnancy included compounds not previously reported, including dihydroorotate, phenol glucuronide, 7,8-dihydroneopterin, nicotinate ribonucleoside, lanthionine, and dopamine.[18,19,20,22,23,24] The present study also differed in that it did not select valine, tryptophan, purine or steroid metabolites.[17,19,20] As reported previously, GDM perturbed biochemicals related to arginine, lysine, citrate, and fatty acid metabolism.[17,18,22,23,24]

Six of the selected 11 (54.5%) compound candidates are related to amino acid catabolism (n=3), glucose oxidation (n=1), and fatty acid oxidation (n=2). Three other compounds are involved in antioxidant pathways, likely reflecting hyperglycemia-associated oxidative stress and inflammation.[7,25,26,27] All together these findings are consistent with the metabolic disruptions of insulin resistance and diabetes as early as the first trimester. Interestingly, a small longitudinal GDM study documented some reduction in insulin-stimulated glucose disposal prior to conception.[28]

A previous metabolomics study reported the predictive value of 17 metabolites in serum collected at about 16 weeks' gestation.[17] Comprising fatty acids, sugars, and amino acids, this panel predicted GDM with a ROC area of 0.8485, a sensitivity of 78%, specificity of 75%, and accuracy of 76.5%. In serum obtained at about 12 weeks' gestation, PAPP-A, glycine, arginine, isovalerylcamitine, and maternal risk factors had a ROC area of 0.83. sensitivity of 72%, specificity of 80%, and an accuracy of 76%.[18] Another metabolomics study reported ROC areas ranging from 0.641 to 0.858 for single urinary metabolites of tryptophan or purines.[19]

In the present study, the classification tree selected a subset of seven metabolites for identifying GDM. The algorithm's high predictive accuracy (96.7%) was substantially greater than that previously reported for one or more first-trimester biochemicals, even with the addition of maternal risk factors.[16,17,18]

Clinical implications. The results bolster confidence that these advanced analytical methods can potentially create a metabolite model sufficiently accurate for the first trimester diagnosis of GDM. As in type 2 diabetes,[29] mitochondrial dysfunction likely has a critical role in pathogenesis of GDM.[5,6,7,25] Stabilizing mitochondrial function and reducing the generation of reactive oxygen species and pro-inflammatory mediators may enhance insulin sensitivity and improve maternal and fetal outcomes.

Research Implications. Based on variable and unverified screening methods, 15-70% of GDM can be detected <24 weeks' gestation.[30] In a meta-analysis of 13 cohort studies, the perinatal mortality, neonatal hypoglycemia, and insulin requirement were greater for early-onset versus late-onset GDM.[30] However, universal first-trimester screening remains controversial because of the lack of validated methods for early GDM screening/diagnosis, questionable benefit of present interventions and therapeutic targets, and the absence of randomized studies.[30,31] Thus, it is not certain that the benefit of early intervention outweighs the costs of extended glucose monitoring, cost, and patient inconvenience.

That late diagnosed GDM (≥24 weeks gestation) exhibit in early pregnancy a distinctive array of metabolic perturbations presents a strong argument for early diagnosis and intervention. First, the perturbed metabolites impair insulin resistance through direct and indirect effects on insulin sensitivity and metabolism.[32] Second, the disrupted metabolic signaling pathways can alter epigenetic regulatory mechanisms involving transcription factors, chromatin, small RNAs, and DNA methylation.[33] The resulting epigenetic perturbations dysregulate metabolic, cardiovascular, and neuroendocrine pathways.[14]This mechanism has been attributed to adverse fetal programming that, in addition to inherited genetic susceptibility, increases later risk for significant metabolic and cardiovascular disorders. Questions naturally arise regarding GDM: 1) What mechanism(s) trigger dysfunctional insulin resistance and defective β-cell release of insulin? and 2) What therapeutic interventions blunt the gestational progression of the disorder and mitigate fetal epigenetic dysregulation?

The present study indicates that a urinary metabolic phenotype in early pregnancy can accurately identify GDM subsequently diagnosed in early or late pregnancy, enabling randomized, innovative interventions (including dietary enhancement of mitochondrial function[29]) targeting short- and long-term perinatal morbidity. A validation metabolomics study would further support the high diagnostic accuracy of this promising model, which could replace the GCT and GTT. Validation will also allow urinary measurements to be restricted to model metabolites, reducing cost. This achievement will enable longitudinal studies on whether regulating the material metabolic milieu from early pregnancy will diminish GDM prevalence, perinatal morbidity, and the long-term risks of obesity, type 2 diabetes, and cardiovascular disease.

Strengths and Limitations. A major strength of the study is the analysis by untargeted metabolomics, a powerful tool for identifying biomarkers. Furthermore, the expanded analysis platform measured a large scope of metabolites, facilitating discovery of those independently associated with GDM.

Another distinct advantage is the use of advanced multivariate methods not previously utilized for metabolomics studies in GDM. When there are many variables (626 metabolites in present study) and a few observations (two in present study), conventional logistic regression or discriminant analysis suffers from overfitting and high error rates when used to find important variables from the candidate pool. For a very large number of metabolites compared to observations, conventional regression is not even feasible.

Therefore, random forest predictive accuracy, random forest GINI worsening, and gradient boost model were used for multivariate analysis. Using a consensus of the two models (random-forest, gradient-boost model) with different assumptions regarding linearity and additivity and selecting only those metabolites identified as strong predictors by both methods provided additional protection against false positives[17] and a smaller subset of metabolites for consideration in the predictive algorithm. This consensus analysis bolstered confidence in the identifying true positives albeit at the likely expense of increasing false negatives.

With 46 case-control pairs, the study size was insufficient to provide separate training and validation. The relatively small size of the study and the uneven representation of ethnic groups also restricts application to the general application. Thus, this study requires validation in a larger, ethnically diverse population. The lack of standardized diagnostic criteria was suboptimal; however, this reflected community practice. This inconsistency did not significantly impair diagnostic accuracy, because oral hypoglycemic therapy was required in 65% (11/17) of those with GDM identified by unconventional criteria (lower GTC threshold, $HbA_1c$).

Conclusions. Advanced analytical methods have identified for the first time a maternal metabolite profile as early as the first trimester that accurately predicted GDM diagnosed in both early and late gestation. Validation of the model by a larger study will support 1) a urinary metabolic phenotype as an alternative to the GCT and GTT for GDM diagnosis, and 2) clinical investigations to determine to what extent normalizing maternal metabolism in the first trimester reduces GDM prevalence, perinatal morbidity, and fetal epigenetic disruptions that contribute to the growing surge in obesity, type 2 diabetes, and cardiovasculardisease.

REFERENCES

1. Catalano P M, et al. Am J Obstet Gynecol 1991; 165(6 pt 1):1667-1667-72.
2. Zhu Y, Zhang C. Curr Diab Rep 2016; 16(1):7.
3. American College of Obstetricians and Gynecologists. ACOG Practice Bulletin. Clinical management guidelines for obstetrician-gynecologists. Number 190. Obstet Gynecol 2018; 131:e49-e63.
4. Poolsup N, et al. PLoS One 2014; 9:e92485
5. Ma RCW, et al. Prog Biophys Mol Biol 2015; 118:55-68.
6. Briana D D, et al. J Matem Fetal Neonatal Med 2018; 31(7):895-900.
7. Sallam N A, et al. IntJ Mol Sci 2018; 19(11), 3365.
8. Atig M, et al. Pediatr Cardiol 2017; 38(5):941-45.
9. Lowe W L, et al. Diabetologia 2019; 62:598-610.
10. Alexander B T, et al. Compr Physiol 2015; 5(2):997-1025.
11. Monteiro L, et al. Placenta 2016; 48(Suppl 1):S54-S60.
12. Goyal D, et al. J Endocrinol 2019; 242:T105-T119.
13. Elliott H R, et al. Diabetologia 2019; 62:2171-2178.
14. Haertle L, et a. Clin Epigenetics 2017; 9:28.
15. Cvitic S, et al. Diabetologia 2018; 61:2398-2411.
16. Powe C E. et al. Curr Diab Rep 2017; 17:12.
17. Enquobahrie D A, et al. J Clin Endocrinol Metab 2015; 100:4348-56.
18. Nevalainen J, at al. Rev Diabet Stud 2016 Winter; 13(4):236-45.
19. Law K P, et al. Clin Chim Acta 2017; 468:126-39.
20. Liu X, at al. Sci Rep 2019; 9:2605.
21. Ford L, et al. J Appl Lab Med 2020; 5(2):342-56.
22. Sachse D, at al. PLoS One 2012; 7(12):e52399.
23. Qiu C, et al. Diabetes Res Clin Pract 2014; 104:393-400.
24. White S L, et al. Diabetologia 2017; 60(10):1903-12.
25. Plows J F, et al. Int J Mol Sci 2018; 19(11):3342.
26. Rehman K, et al. J Cell Biochem 2017; 118(11):3577-3578.
27. Radaelli T, et al. Diabetes 2003; 52(12):2951-2958.
28. Catalano P M, at al. Am J Physiol 1993; 264:E60-E67.
29. Sergi D, et al. Front Physiol 2019; 10:532.
30. Immanuel J, Simmons D. Curr Diab Rep 2017; 17(11):115.
31. Placencia W, et a. Fetal Diagn Ther 2011; 30(2):108-115.
32. Yang Q, et al. Nat Rev Med Cell Biol. 2018; 19(10):654-672.
33. Sharma U, Rando O J. Cell Metab 2017; 25:544-558.

Example 2: Urinary Metabolites Greater than 20 Weeks of Gestation Predict Gestational Diabetes Mellitus This study was undertaken 1) to assess whether the relative levels of late pregnancy, urinary metabolites of GD differ to those of normal gravidas (NG), and 2) to determine whether the proposed distinctive metabolites in randomly collected urine have utility to identify GD in the latter half of gestation.

Methods: This nested observational case-control study involved 46 GD and 46 NG, who were matched for maternal age, pre-pregnancy BMI and gestational age at urine collection. Exclusion criteria included multiple gestation, metabolic or cardiovascular disorders. The Global Alliance to Prevent Prematurity and Stillbirth supplied the urine samples and demographic data. Practitioners at three separate medical centers diagnosed GD by glucose challenge and glucose tolerance tests according to local criteria. A metabolomics platform (Metabolon, Inc.) analyzed the osmolality corrected levels of 626 untargeted endogenous metabolites (<1,000 Daltons) in urine. Multivariate methods (random forest accuracy and GINI, boosting relative importance) screened for metabolites simultaneously distinguishing GD from NG. A classification tree provided the final algorithm for predicting GD vs NG.

Results: The case and control groups were similar with respect to material age (MA), pre-pregnancy body mass index (BMI), and gestational age (GA) at urine collection (mean, (SD)). These characteristics are summarized in Table 4.

TABLE 4

| | MA (years) | BMI (kg/m$^2$) | GA (weeks) |
|---|---|---|---|
| Gestational Diabetes | 32.2 (4.7) | 31.5 (6.8) | 30.8 (3.6) |
| Normal Gravidas | 31.8 (4.2) | 29.9 (6.3) | 30.5 (3.0) |

Figure 3:
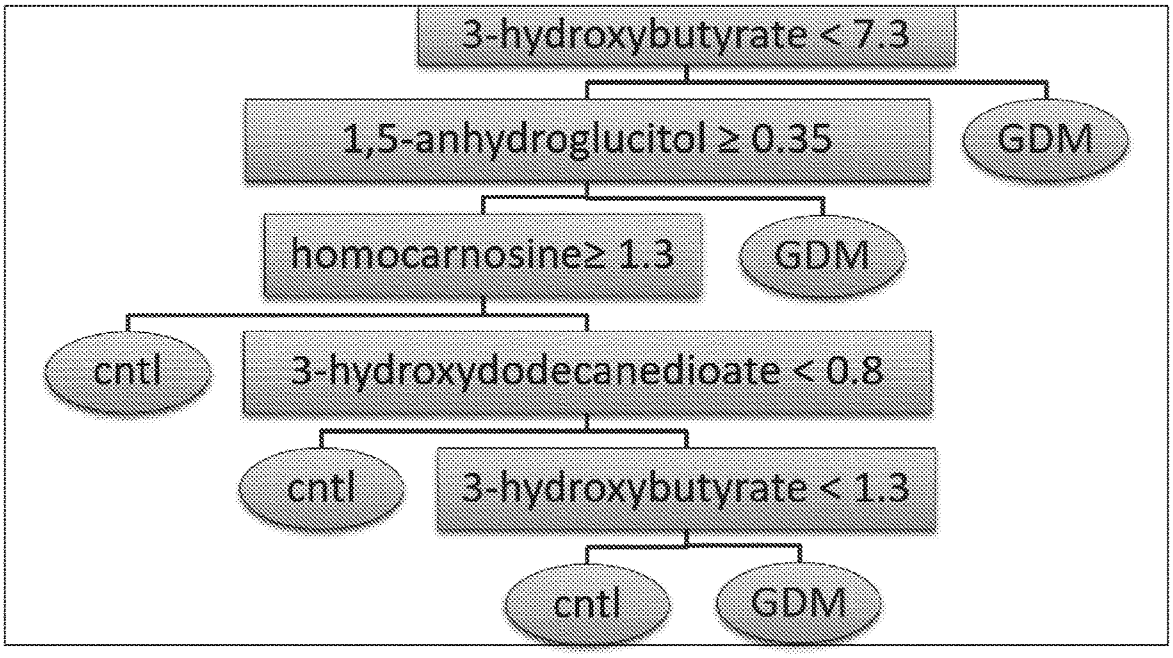
FIG. 3 illustrates a classification tree for 2nd and 3rd trimester subjects, using osmolality normalized urine metabolite measurements. Yes=left branch, No=right branch.

Three multivariate criteria simultaneously identified eight metabolites distinguishing GD vs NG. A five-level classification tree incorporating 4 of these metabolites (3-hydroxybutyrate, 1,5-anhydroglucitol, homocamosine, 3-hydroxydodecanedioate) predicted GDM with an unweighted accuracy (average of sensitivity and specificity) of 89%. The classification tree is shown in FIG. 3.

This Example reveals that the metabolic profile of random urine samples in the latter half of pregnancy was highly accurate in identifying GD vs NG. The numbers refer to osmolality corrected concentration units.

Example 3: Gestational Diabetics have Perturbed Energy Metabolism in Early Pregnancy Gestational diabetics (GD) have impaired insulin sensitivity prior to conception. The objective of this Example was to determine whether maternal urinary metabolites in early pregnancy reveal altered metabolic pathways.

Methods: This nested, observational case-control cohort study consisted of randomly collected, de-identified urine samples from the Global Alliance to Prevent Prematurity and Stillbirth (Seattle, WA). The glucose challenge and glucose tolerance tests diagnosed GD by institutional criteria. The study consisted of 46 GD and 46 controls (NG) with singleton gestations matched by maternal age, body mass index (BMI), and gestational age (GA) at urine collection. Excluded gravidas had significant metabolic or cardiovascular disorders. An unbiased metabolomics platform (Metabolon, Inc.) analyzed the osmolality corrected concentrations of 626 endogenous urinary compounds (<1,000 Daltons). Multivariate methods (random forest, boosting relative importance) identified metabolites that differentiated simultaneously GD from NG.

Results: The case and control groups had similar mean maternal age [GD: 32 t 0.7 (SE); NG: 32 t 0.6 years], prepregnancy body mass index (GM: 31.5±1.0; NG 30.0±1.0 kg/m$^2$), and gestational age (GD: 11.7±0.4; NG: 12.0±0.4 weeks) at urine collection. Multivariate criteria identified 26 compounds simultaneously distinguishing GD vs control. Pathway analysis indicated that GD altered pathways of nitrogen balance (n=7), oxidation-reduction (n=8), and oxidative phosphorylation (n=5). Changes in microbiome-derived metabolites (n=7) included cognates of bile acids (3), lysine (2), and phenylalanine (2).

GD exhibit in early pregnancy perturbations in metabolic pathways that are consistent with increased oxidative stress, disrupted energy metabolism, and insulin resistance.

Example 4: Urinary Metabolites Identified in Early Pregnancy Also Predict GDM in Late Pregnancy Urine (>20 Weeks' Gestation)

Figure 4:
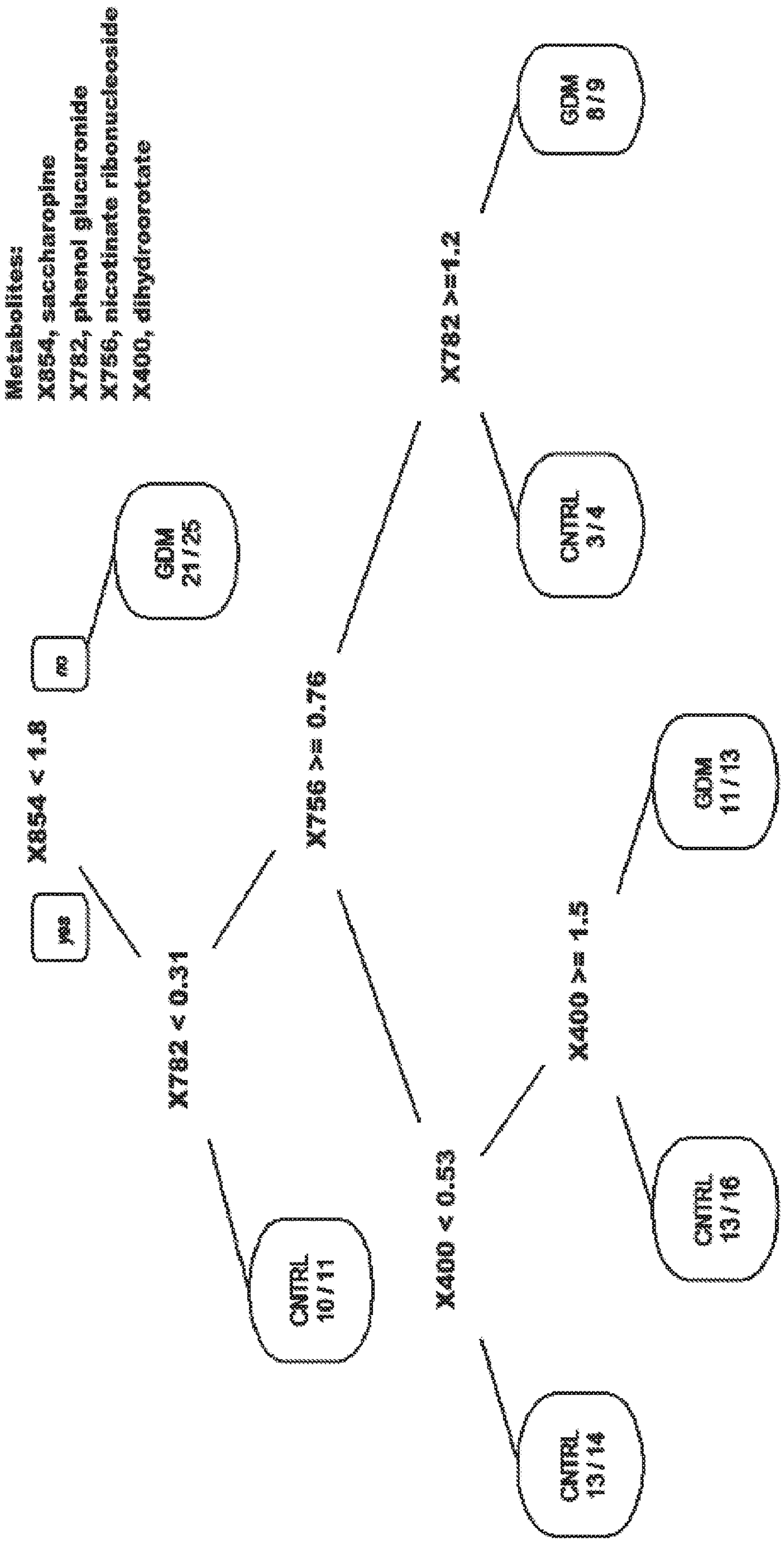
FIG. 4 illustrates a classification tree for 2nd trimester subjects using metabolites found in the 1st trimester study, n=46 pairs, osmolality normalized urine metabolite measurements. Metabolites: X854, saccharopine; x782, phenol glucuronide; X756, nicotinate ribonucleoside; X400, dihydroorotate.

This study was undertaken 1) to assess whether the relative levels of late pregnancy, urinary metabolites of GD differ to those of normal gravidas (NG), and 2) to determine whether the proposed distinctive metabolites in randomly collected urine have utility to identify GD in the latter half of gestation. The validating data are shown in FIG. 4, and demonstrate the accuracy of the seven metabolites (used in Example 1 above for <20 weeks gestation) for >20 weeks of gestation (same patients as for Example 2). The classification tree for the seven metabolites is shown below, of which only 4 were found to optimize the accuracy of detecting GDM. The study included 46 pairs of subjects, and the metabolite measurements were osmolality normalized. The metabolites are listed in Table 5, with strike-through indicating those metabolites that were not used, argininate (X304), 7,8-dihydroneopterin (X257), and lanthionine (X622).

TABLE 5

| Metabolite number | metabolite name |
|---|---|
| X400 | dihydroorotate |
| X304 | argininate* |
| X782 | phenol glucuronide |
| X257 | 7,8-dihydroneopterin |
| X756 | nicotinate ribonucleoside |
| X622 | lanthionine |
| X854 | saccharopine |

TABLE 6

| Group | Predicted control | Predicted GDM | total | Pct correct |
|---|---|---|---|---|
| Control | 39 | 7 | 46 | 84.8% |
| GDM | 6 | 40 | 46 | 87.0% |

Nominal equal weight accuracy = 85.9%, C stat = 0.879

The classification table shown in Table 6 indicates the GDM sensitivity of 84.5%; the NG specificity was 87%, and the nominal accuracy was 86%. The area under the curve (AUC) was 0.0.879.

Throughout this application various publications are referenced. The disclosures of these publications in their entireties are hereby incorporated by reference into this application in order to describe more fully the state of the art to which this invention pertains.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method of treating gestational diabetes mellitus (GDM) in a subject, wherein the subject is 6-40 weeks pregnant or postpartum, the method comprising:

(a) measuring the amount of a plurality of metabolic markers present in a test sample obtained from the subject;

(b) measuring an increase or decrease in the amount of the metabolic markers present in the test sample relative to reference levels of the markers;

(c) treating the subject for GDM;

wherein the metabolic markers comprise dihydroorotate, and one or more of: argininate, 7,8-dihydroneopterin, nicotinate ribonucleoside, saccharopine; and lanthionine, wherein the treating comprises administration of an oral hypoglycemia agent, dietary modification, or insulin therapy.

2. The method of claim 1, wherein the measured increase or decrease of metabolic markers in step (b) is a combination of a decrease in dihydroorotate, and an increase in argininate, 7,8-dihydroneopterin, and saccharopine.

3. The method of claim 2, wherein the plurality of metabolic markers comprises each of dihydroorotate, argininate, phenol glucuronide, 7,8-dihydroneopterin, nicotinate ribonucleoside, saccharopine; and lanthionine.

4. The method of claim 2, wherein the plurality of metabolic markers further includes one or more additional markers selected from the group consisting of: dopamine, octanoylcarnitine (c8), 3-methylglutarate/2-methylglutarate, and/or isocitric lactone; and wherein an increase is measured in the additional marker.

5. The method of claim 1, wherein the measured increase or decrease of metabolic markers in step (b) is a combination of an increase in dihydroorotate, phenol glucuronide, and nicotinate ribonucleoside.

6. The method of claim 1, wherein the measured increase or decrease of metabolic markers in step (b) is a combination of an increase in dihydroorotate, phenol glucuronide, nicotinate ribonucleoside, and a decrease in lanthionine.

7. The method of claim 1, wherein the measuring comprises chromatography or spectrometry.

8. The method of claim 7, wherein the chromatography is gas or liquid chromatography.

9. The method of claim 7, wherein the spectrometry is mass spectrometry.

10. The method of claim 1, wherein the subject is 6-40 weeks pregnant.

11. The method of claim 1, wherein the subject is postpartum.

12. The method of claim 1, wherein test sample is urine.

13. The method of claim 12, wherein the plurality of metabolic markers is osmolality normalized.

14. The method of claim 13, wherein the measuring of step (b) is performed according to a classification tree as follows:

(i) the measured level of dihydroorotate is below 0.24, and the sample is assayed for argininate;

(ii) the measured level of argininate is greater than or equal to 0.79, and the sample is assayed for 7,8-dihydroneopterin;

(iii) the measured level of 7,8-dihydroneopterin is greater than or equal to 0.45, and the sample is assayed for saccharopine;

(iv) the measured level of saccharopine is greater than or equal to 1.2; or the measured level of saccharopine is less than 1.2 and the measured level of argininate is less than 0.98;

(v) the measured level of dihydroorotate is greater than or equal to 0.24, and the sample is assayed for phenolglucouronide;

(vi) the measured level of phenolglucouronide is greater than or equal to 0.22, and the sample is assayed for nicotinate ribonucleoside;

(vii) the measured level of nicotinate ribonucleoside is less than 0.75 and lanthionine is less than 0.71;

(viii) nicotinate ribonucleoside is greater than or equal to 0.75 and dihydroorotate is greater than or equal to 1.5.

15. The method of claim 13, wherein the having diabetes is determined measuring of step (b) is performed according to a classification tree as follows:

(i) the measured level of saccharopine is greater than or equal to 1.8;

(ii) the measured level of saccharopine is less than or equal to 1.8, and the sample is assayed for phenol glucuronide;

(iii) the measured level of phenol glucuronide is greater than or equal to 0.31, and the sample is assayed for nicotinate ribonucleoside;

(iv) the measured level of nicotinate ribonucleoside is less than 0.76, and the sample is assayed for phenol glucuronide and the measured level of phenol glucuronide is less than 1.2; or (v) the measured level of nicotinate ribonucleoside is greater than or equal to 0.76, and the sample is assayed for dihydroorotate and the measured level of dihydroorotate is greater than or equal to 0.53 and less than 1.5.

16. The method of claim 1, wherein multivariate statistical analysis and/or a mathematical method is used to determine when the markers are increased or decreased.

17. A non-transitory computer-readable storage medium storing computer-readable algorithms, instructions or codes that, when executed by a computing device comprising at least one processor, cause or instruct the at least one processor to perform the method of claim 1.

18. A method of treating gestational diabetes mellitus (GDM) in a subject, wherein the subject is 6-40 weeks pregnant or postpartum, the method comprising:

(a) measuring the amount of a plurality of metabolic markers present in a test sample obtained from the subject;

(b) measuring an increase or decrease in the amount of the metabolic markers present in the test sample relative to reference levels of the markers;

(c) treating the subject for GDM;

wherein the plurality of metabolic markers comprises 3-hydroxybutyrate, 1, 5-anhydroglucitol, homocarnosine, and 3-hydroxydodecanedioate, wherein the plurality of metabolic markers predict GDM diabetes with an accuracy of 89%;

wherein the treating comprises administration of an oral hypoglycemia agent, dietary modification, or insulin therapy.

19. The method of claim 18, wherein the test sample is urine and the measured metabolic markers are osmolality normalized, and wherein the measuring of step (b) is performed according to a classification tree as follows:

(i) the measured level of 3-hydroxybutyrate is greater than or equal to 7.3;

(ii) the measured level of 1,5-anhydroglucitol is less than 0.35;

the measured level of 1,5-anhydroglucitol is greater than or equal to 0.35, and the sample is assayed for homocarnosine and the measured level of homocarnosine is greater than or equal to 0.8, and the sample is assayed for 3-hydroxydodecanedioate, and the measured level of 3-hydroxybutyrate is greater than or equal to 1.3.

* * * * *